United States Patent

Kempf et al.

[11] Patent Number: 5,833,462
[45] Date of Patent: Nov. 10, 1998

[54] PRECISION ATTACHMENTS FOR DENTAL TECHNOLOGY CAPABLE OF BEING CAST ON

[75] Inventors: Bernd Kempf, Kleinwallstadt; Hans Martin Ringelstein, Frankfurt; Alexander Voelcker, Rodenbach; Ulrich Birkholz, Hanau, all of Germany

[73] Assignee: Degussa Aktiengesellschaft, Frankfurt am Main, Germany

[21] Appl. No.: 606,265

[22] Filed: Feb. 23, 1996

[30] Foreign Application Priority Data

Feb. 25, 1995 [DE] Germany .................. 195 06 681.2

[51] Int. Cl.⁶ .................................................. A61K 6/04
[52] U.S. Cl. ............................................ 433/207; 420/507
[58] Field of Search ............................. 433/207; 420/507

[56] References Cited

U.S. PATENT DOCUMENTS

| | | | |
|---|---|---|---|
| 1,022,596 | 4/1912 | Rossi | 420/507 |
| 4,381,955 | 5/1983 | Desai | 420/507 |
| 4,606,981 | 8/1986 | Mizuhara | 420/507 |
| 4,684,555 | 8/1987 | Neumeyer | 433/220 |
| 4,806,306 | 2/1989 | Groll et al. | 433/207 |
| 4,808,373 | 2/1989 | Hoffman et al. | 420/507 |
| 5,139,739 | 8/1992 | Takayanagi et al. | 420/507 |
| 5,362,438 | 11/1994 | van der Zel | 433/207 |
| 5,423,680 | 6/1995 | Prasad | 420/507 |
| 5,453,290 | 9/1995 | van der Zel | 433/207 |
| 5,518,691 | 5/1996 | Muragishi et al. | 420/507 |

FOREIGN PATENT DOCUMENTS

| | | |
|---|---|---|
| 190648 | 8/1986 | European Pat. Off. . |
| 691123 | 1/1996 | European Pat. Off. . |
| 609883 | 2/1935 | Germany . |
| 2052749 | 5/1972 | Germany ................. 420/507 |
| 2357552 | 5/1975 | Germany . |
| 3812568 | 11/1989 | Germany . |
| 4306542 | 1/1993 | Germany . |
| 4419408 | 7/1995 | Germany . |
| 90948 | 6/1982 | Japan ....................... 420/507 |

OTHER PUBLICATIONS

Graham, Precipitation hardening in Gold–Titanium Alloys, Proceedings Thirty–First Annual Meeting Electron Microscopy Society of America, Edited by Arceneaux, Claitor's Publishing Division Baton Rouge, Louisanna, pp. 148, 149, 1973.

Hansen, Phil, *Constitution of Binary Alloys*, 1958, pp. 237–239.

*Primary Examiner*—Ralph A. Lewis
*Attorney, Agent, or Firm*—Beveridge, DeGrandi Weilacher & Young, LLP

[57] ABSTRACT

Precision attachments containing a titanium-containing gold alloy which is covered with a gold film, capable of being cast on, which have a golden yellow color, are extremely corrosion-resistant and, despite base metal constituents, form no oxides at the place of casting-on.

3 Claims, 3 Drawing Sheets

PRECISION ATTACHMENTS FOR DENTAL TECHNOLOGY CAPABLE OF BEING CAST ON

INTRODUCTION AND BACKGROUND

The present invention relates to precision attachments for dental technology capable of being cast on, which attachments are made of noble metal alloys containing oxide-forming base metals.

In the manufacture of removable dental devices or appliances, a suitable connecting technique, which makes possible the connection of the dental device with the remainder of the denture or also with dental implants, is frequently required. Parts manufactured by assembly line, so-called precision attachments, such as attachments, bridge anchors or root pins or posts are increasingly used for this purpose (for more information on dental attachments see Ullmann's Encyclopedia of Industrial Chemistry, 5th Edition, volume A8, pages 251 et seq (Dental Materials), especially pages 265–266 (all incorporated by reference); Elephant Attachments Type Piccolo (Elephant edelmetaal, Hoorn, Holland); Degussa Ceramic Alloys (MD 193-14-15-485 TD; Degussa AG, Frankfurt, Germany); Glossary of Prosthodontic Terms, J. Prosthet. Dent., volume 38, number 1 (July 1977), page 71). The parts are brazed or cast onto the metallic dental attachment. The technique of casting-on is increasingly preferred in this connection to brazing, since the introduction of another alloy as a solder can thereby be avoided with favorable effect on the corrosion resistance.

The connection is made in both cases by metallurgical processes, i.e. by forming an alloy between a liquid and a solid metallic phase. This may, however, be limited to a reaction zone extending over only a few atomic layers. In the case of the casting-on technique, the cast-on alloy itself takes over the role of the solder.

In order, during the casting-on process, to obtain a real material composite between the precision attachments and the cast-on alloy, coatings in the form of oxides or other compounds must not be formed during the preheating of the precision attachments. Previously, therefore, only alloys containing no oxidizable constituents, that is no base metals, were used in the precision attachments. The alloys used in making the precision attachments must in addition have adequate strength and a melting range which is distinctly above that of the alloy to be cast on in order that the precision attachments shall not begin to melt during the casting-on process.

Gold-based alloys with high palladium and platinum contents therefore have been used. Typical alloys have compositions with about 60 wt. % gold, about 25 wt. % platinum and about 15 wt. % palladium. Alloys with about 80 wt. % platinum and 20 wt. % iridium are also used. In DE-OS 35 42 641 (corresponding to U.S. Pat. No. 4,806,306 which is incorporated by reference in its entirety), for example, an alloy is described which consists of 40 to 70% platinum, 10 to 40% palladium, 5 to 20% iridium and 0.5 to 10% gold.

All alloys previously used for constructional elements capable of being cast on have a white color and a very low coefficient of thermal expansion (CTE) because of their high proportions of platinum group metals. In the conventional alloys to which porcelain can be fused, with CTE values of about $14 \times 10^{-4}/°$ C., this was still acceptable or unavoidable.

New golden-yellow alloys to which porcelain can be fused, having a CTE value of about $17 \times 10^{-6}/°$ C. which can be veneered with a special low-melting dental ceramic, have recently been on the market. The alloys capable of being cast on that are available at present are unsuitable for this alloy. Apart from the clear difference in the color of the alloy, the considerably larger difference in CTE between the alloys is especially disadvantageous. The large CTE difference easily leads to fissuring in the dental ceramic, which has a CTE value matched to the yellow alloys and therefore higher than that of the conventional dental ceramics.

For these golden yellow alloys to which porcelain can be fused, precision attachments of yellow alloys are desirable, in order that these do not contrast in color with the base material. Previously, all these yellow alloys were alloyed with base metals and therefore could not be cast on. Their composition is generally based on gold-platinum-silver-copper and they largely owe their mechanical strength to the silver-copper miscibility gap. As a result of the relatively high copper content caused thereby, there is potentially a tendency to discoloration, especially where a crevice corrosion situation exists. In addition, when the precision attachments is heated in air, the copper forms oxides, which impede a casting-on.

SUMMARY OF THE INVENTION

One object of the present invention was to provide precision attachments for dental technology capable of being cast on, which are made of noble metal alloys containing oxide-forming base metals, have a golden yellow color, are extremely corrosion resistant and are matched in coefficient of thermal expansion to the casting-on alloy and above all form no oxide films at the place of casting-on.

This and other objects are achieved according to the present invention by forming the precision attachments from a titanium-containing gold alloy and coating with a gold (24K) film. The gold alloy preferably contains 0.5 to 4 wt. % titanium. It can also contain in addition up to 40 wt. % silver, up to 10 wt. % palladium and/or platinum and up to 3 wt. % of one or more of the base metals copper, zinc, indium, tin, niobium, tantalum, tungsten, germanium and iron.

BRIEF DESCRIPTION OF THE DRAWINGS

The present invention will be further understood with reference to the drawing, wherein.

DETAILED DESCRIPTION OF THE INVENTION

According to a more detailed aspect of the invention, it is furthermore advantageous if only the place of casting-on of the precision attachments bears a partial gold film, the thickness of which is preferably between 3 and 100 µm.

In principle, a series of methods are suitable for the application of the gold film, the method and the minimum film thickness to be applied having always to be optimally adapted to the particular alloy. Suitable processes for the preparation of the film are electrodeposition, roll-bonded cladding or the etching out of oxidizable alloy constituents by a suitable pickle. Such methods are known in the art.

In the case of precision attachments of gold with 0.5 to 4 wt. % titanium, to which films of pure gold are applied, oxidation of the precision attachments has proved to be reliably prevented. Even gold films with a thickness of 3 μm are adequate for this purpose. During the heat treatment occurring during the casting-on there is also a hardening of the gold film, so that the material composites have a high bonding strength.

The use of these alloys is not limited to the manufacture of attachments, but it can also be extended to other parts and to other fields of application.

The attachment may be in the form of a shaped body for use in the field of dental technology and adapted to connect to a dental prosthesis. The attachment comprises a titanium-containing gold alloy which contains 0.5 to 4 wt. % titanium, up to 40 wt. % silver, up to 10 wt. % palladium and/or platinum, up to 3 wt. % of one or more of the base metals selected from copper, zinc, indium, tin, niobium, tantalum, tungsten, germanium, iron or mixtures thereof, and the balance being gold. The attachment may be in the form of a root post used to anchor crowns and bridges in dental technology.

Examples of the coefficient of thermal expansion (CTE) and melting point of the titanium-containing gold alloy of the present invention are as follows:

| Alloy | CTE [$\times 10^{-6}$] | Melting Point |
| --- | --- | --- |
| 98.3 wt. % Au, 1.7 wt. % Ti | 15.0 | about 1080° C. |
| 98.8 wt. % Au, 1.2 wt. % Ti | 15.1 | about 1070° C. |
| 97.2 wt. % Au, 2.8 wt. % Ti | 14.7 | about 1100° C. |

Figure 1:
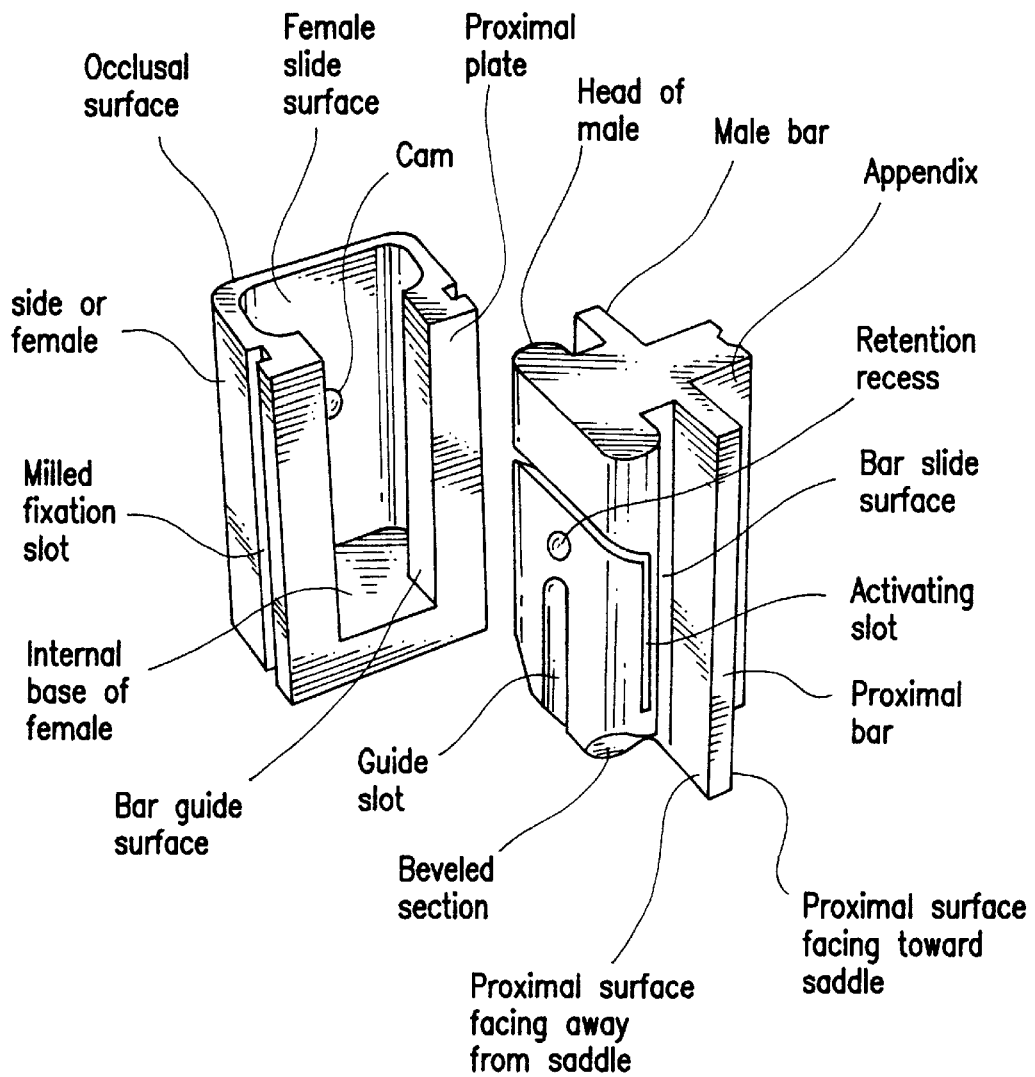
FIGS. 1–3 show precision attachments, such as attachments, bridge anchors or root pins or posts, which can be formed from the alloy of the present invention.
Figure 2:
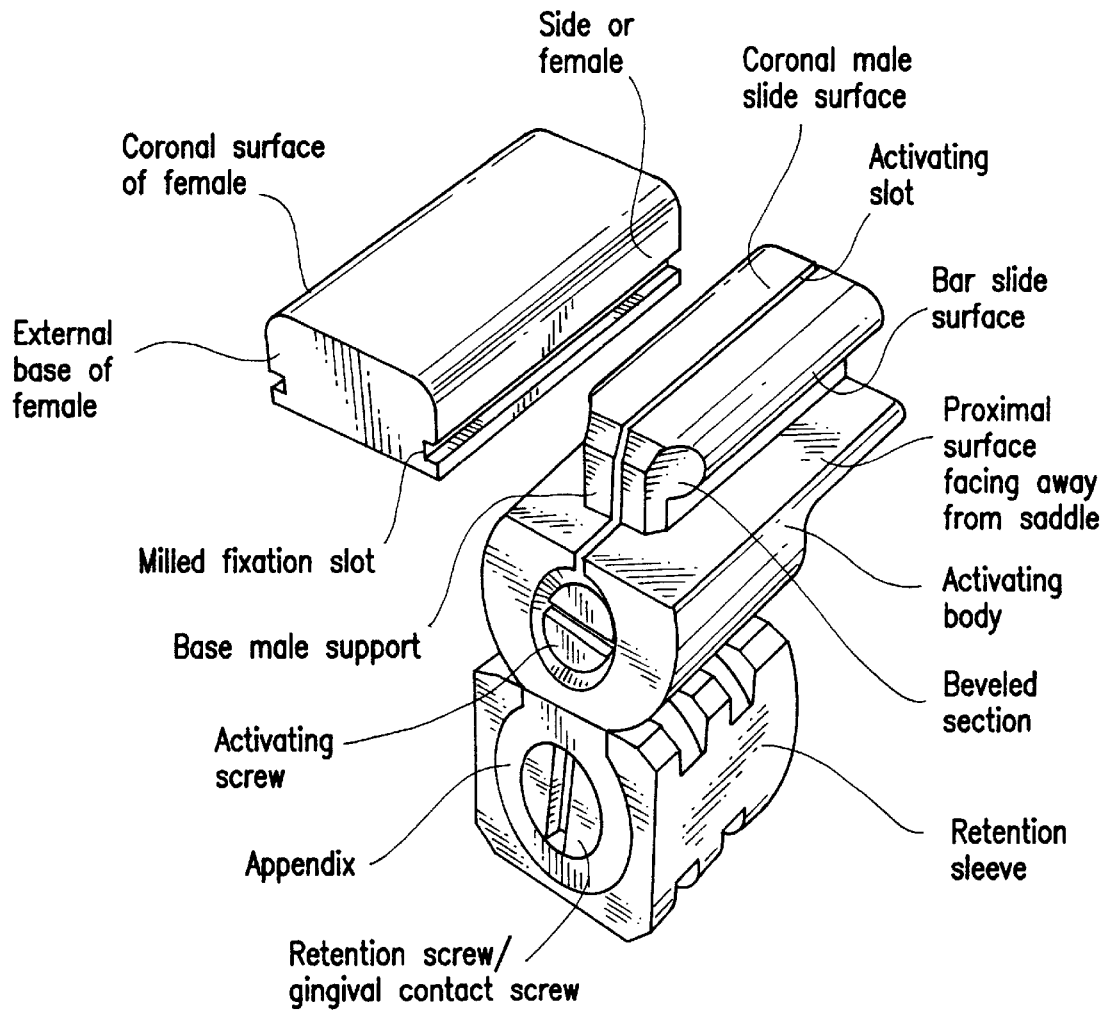
Figure 3:
Figure 3:
Figure 3:
Figure 3:
Figure 4:
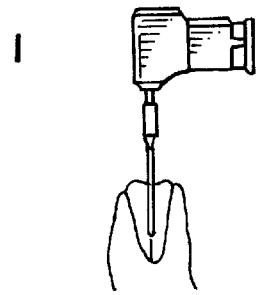
FIG. 4 shows how a root post made of the alloy of the present invention can be used by a dentist.
Figure 4:
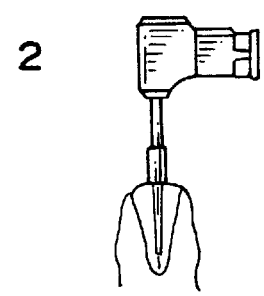
Figure 4:
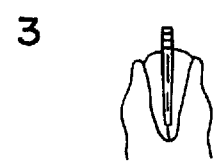
Figure 4:

FIGS. 1 and show an activatable T-attachment and a fine-adjustable T-attachment with interchangeable mate which can be formed from the alloy of the present invention. FIG. 3 shows root posts which can be formed from the alloy of the present invention: top (smooth root post-tapered root post without thread, used for cast thimbles and root caps to hold precision attachments), middle (root post for Biodent crowns-conical root post with head retention without thread, used for cast thimbles and root caps to hold precision attachments), bottom (parapin-parapulpic for biocompatible deep anchoring, used for parapulpic deep anchoring of cast, ceramic, and composite fillings, partial crowns-pinlay, pinledge, root caps). FIG. 4 shows how a root post made of the alloy of the present invention can be used by a dentist: (1) After the root canal treatment has been completed, the next step is mechanical predrilling with the pilot drill. (2) With the root canal trimmer, the predrilled root canal is expanded to the size of the desired root post (small, medium, large). During this step, the lowering depth is marked by a previously emplaced silicone stop which was positioned with the root canal trimmer in the corresponding depression in the depth gauge. (3) Then the temporary posts can be positioned to support the provional treatment. The impression-taking is carried out with the original posts. When the cast root post thimpble is available, the root canal is filled with cement during a second appointment. Remove the excess cement.

The following examples are intended to illustrate the invention in more detail:

Example 1: From a gold-titanium alloy having a titanium content of 2 wt. %, a melting range of 1120°–1090° C. and a CTE of 15.0×10$^6$/° C., a root pin is produced, which is subsequently electrocoated with a gold film of about 20 μm thickness. Onto this root pin there is cast a yellow low-melting alloy of the composition (in wt. %) Au 73.8, Pt 9, Ag 9.2, Cu 4.4, Zn 2, In 1.5, Ir 0.1, with a melting range of 990°–900° C. and a CTE of about 17×10$^4$/° C. An excellent material composite is formed. During the finishing, the dental attachment is in addition ground so far that the root pin material is exposed. Nevertheless, this place is scarcely recognizable by color. The subsequent ceramic veneering also leads to no problems of any kind.

Example 2: By means of roll-bonded cladding a 40 μm thick gold foil is applied to a yellow alloy of the composition (in wt. %) Au 95.1, Cu 3, Ti 1.9. Thereafter constructional elements, which retain their oxidation-protective layer of gold in the designated casting-on areas, are worked with cutting methods out of the semifinished material. The low-melting yellow alloy of Example 1 is cast onto these precision attachments. The two alloys scarcely contrast with each other by color and can be veneered without difficulty with a low-melting ceramic at 800° C.

Further variations and modifications of the foregoing will be apparent to those skilled in the art and such variations and modifications are intended to be encompassed by the claims that are appended hereto.

German Priority Application 195 06 681.2 and 195 06 680.4 filed on 25 Feb. 1995 and 196 04 827.3 filed on 12 Feb. 1996 are relied on and incorporated by reference in their entirety. Our U.S. patent application Ser. No. 604,127 entitled "Use Of Gold Alloys For Precision Attachments In Dental Technology", filed on 20 Feb. 1996, is relied on and incorporated by reference in its entirety.

We claim the following:

1. A method of forming a material composite dental device comprising;

casting on a dental alloy to a precision attachment of titanium-containing gold alloy covered with a gold film wherein the melting point of the dental alloy is below the melting point of the dental attachment.

2. A method of forming a material composite dental device comprising;

casting on a dental alloy to a precision attachment of titanium-containing gold alloy further comprising 40 wt. % or less silver, 10 wt. % or less palladium and/or platinum and 3 wt. % or less of one or more base metals selected from the group consisting of copper, zinc, indium, tin, niobium, tantalum, tungsten, germanium and iron or mixtures thereof and the balance being gold which has thereon a gold film wherein the melting point of the dental alloy is below the melting point of the dental attachment.

3. A method of forming a material composite dental device comprising;

casting on a dental alloy to a precision attachment of titanium-containing gold alloy further comprising 0.5 to 4 wt. % titanium, 40 wt. % or less silver, 10 wt. % or less palladium and/or platinum and 3 wt. % or less of one or more base metals selected from the group consisting of copper, zinc, indium, tin, niobium, tantalum, tungsten, germanium and iron or mixtures thereof and the balance being gold wherein the melting point of the dental alloy is below the melting point of the dental attachment.

* * * * *